United States Patent
Boehmer et al.

(10) Patent No.: US 6,303,838 B1
(45) Date of Patent: Oct. 16, 2001

(54) SEPARATING 1,1,1,3,3-PENTAFLUOROPROPANE FROM HYDROGEN FLUORIDE

(75) Inventors: Sara W. Boehmer, Newark, DE (US); Barry Asher Mahler, Glen Mills, PA (US); Ralph Newton Miller, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/509,859

(22) PCT Filed: Oct. 16, 1998

(86) PCT No.: PCT/US98/21949

§ 371 Date: Mar. 31, 2000

§ 102(e) Date: Mar. 31, 2000

(87) PCT Pub. No.: WO99/20585

PCT Pub. Date: Apr. 29, 1999

Related U.S. Application Data

(60) Provisional application No. 60/062,277, filed on Oct. 17, 1997.

(51) Int. Cl.[7] .................................................. C07C 17/38
(52) U.S. Cl. ............................................ 570/178; 570/180
(58) Field of Search ...................................... 570/177, 180, 570/178

(56) References Cited

FOREIGN PATENT DOCUMENTS

| 95/27689 | * | 10/1995 | (WO) . |
| 97/03936 | * | 2/1997 | (WO) . |
| 97/05089 | * | 2/1997 | (WO) . |

* cited by examiner

*Primary Examiner*—Alan Siegel
(74) *Attorney, Agent, or Firm*—James E. Shipley

(57) ABSTRACT

Disclosed are processes for separating 1,1,1,3,3-pentafluoropropane (HFC-245fa) from hydrogen fluoride (HF) by distillation, wherein hydrocarbons, chloroflurocarbons, hydrochlorofluorocarbons and fluorocarbons are used as entraining agents. The processes comprise: contacting a first mixture comprising HFC-245fa and HF with an entraining agent selected from the group consisting of hydrocarbons, chlorofluorocarbons, hydrochlorofluorocarbons and fluorocarbons to form a second mixture, distilling the second mixture and thereby separating the HFC-245fa from HF and entraining agent, and recovering HFC-245fa substantially-free of HF.

8 Claims, 9 Drawing Sheets

SEPARATING 1,1,1,3,3-PENTAFLUOROPROPANE FROM HYDROGEN FLUORIDE

CROSS REFERENCE TO RELATED APPLICATIONS

This application is a 371 of PCT/US98/214499 filed Oct. 16, 1998 which claims the priority benefit of U.S. Provisional Application No. 60/062277, filed Oct. 17, 1997.

FIELD OF THE INVENTION

The present invention relates to processes for separating 1,1,1,3,3-pentafluoropropane (HFC-245fa) from hydrogen fluoride (HF) by distillation, wherein hydrocarbons, chlorofluorocarbons, hydrochlorofluorocarbons and fluorocarbons are used as entraining agents.

BACKGROUND OF THE INVENTION

New regulations have been established to protect the stratospheric ozone layer from possible damage by chlorofluorocarbons (CFCs). 1,1,1,3,3-Pentafluoropropane ($CF_3CH_2CHF_2$, HFC-245fa) is a hydrofluorocarbon (HFC) which may be used either alone or in blends with other materials as a non-ozone depleting replacement for CFCs. HFC-245fa may be prepared by fluorinating appropriate halopropanes or propenes with hydrogen fluoride (HF). For example, HFC-245fa may be prepared by fluorinating 1-chloro-3,3,3-trifluoropropene in the presence of antimony pentachloride catalyst as is described in U.S. Pat. No. 5,616,819. The HFC-245fa product may contain a variety of impurities such as by-product hydrogen chloride (HCl) and fluorocarbon by-products, as well as unreacted chlorinated precursors and hydrogen fluoride (HF). The presence of HF in HFC-245fa product is objectionable for most uses of HFC-245fa. While most of these impurities can be removed from HFC-245fa by conventional distillation, HF is difficult to remove by conventional distillation because HF and HFC-245fa form an azeotrope. This azeotrope is disclosed in World Intellectual Property Organization publication WO 97/5,089. Due to the formation of the HF/HFC-245fa azeotrope, it is difficult, if not impossible, to completely separate HFC-245fa and HF by conventional distillation to produce streams of HFC-245fa or HF that are substantially-free of the other compound.

The use of conventional methods for removing the HF, such as scrubbing the HFC-245fa with water or in water/caustic solutions, causes loss of the utility of the HF for further reaction and incurs significant product loss due to the high solubility of HFC-245fa in water.

Where many organic compounds form an azeotrope with HF, it is sometimes possible to effect a phase separation by condensing and cooling the mixture, wherein the mixture separates into two liquid phases, one comprising increased HF concentration and the other comprising increased organic concentration relative to the HF and organic concentrations in the azeotrope. Such methods typically do not produce substantially-pure fractions of either HF or organic. Further, mixtures of HF and HFC-245fa do not exhibit such phase separation even when cooled below −25° C.

World Intellectual Property Organization publication WO 97/05089 discloses azeotropic distillation processes for separating HFC-245fa and HF. To obtain high purities and high-recovery-efficiencies of HFC-245fa and HF, these methods require distillating the HFC-245fa and HF-containing streams successively at divergent pressures, which is extremely expensive in practice. It is difficult to obtain HFC-245fa and/or HF substantially-free of the other component by such a method.

SUMMARY OF THE INVENTION

The present invention comprises processes for separating 1,1,1,3,3-pentafluoropropane (HFC-245fa) from hydrogen fluoride (HF), comprising:

contacting a first mixture comprising 1,1,1,3,3-pentafluoropropane (HFC-245fa) and hydrogen fluoride (HF) with an entraining agent to form a second mixture, distilling the second mixture and thereby separating the 1,1,1,3,3-pentafluoropropane (HFC-245fa) from hydrogen fluoride (HF) and entraining agent, and recovering 1,1,1,3,3-pentafluoropropane (HFC-245fa).

BRIEF DESCRIPTION OF THE DRAWINGS

FIG. 7 is a graphical representation at about +20° C. of an azeotropic and azeotrope-like composition formed between HF and CFC-114a.

DETAILED DESCRIPTION

Figure 1:
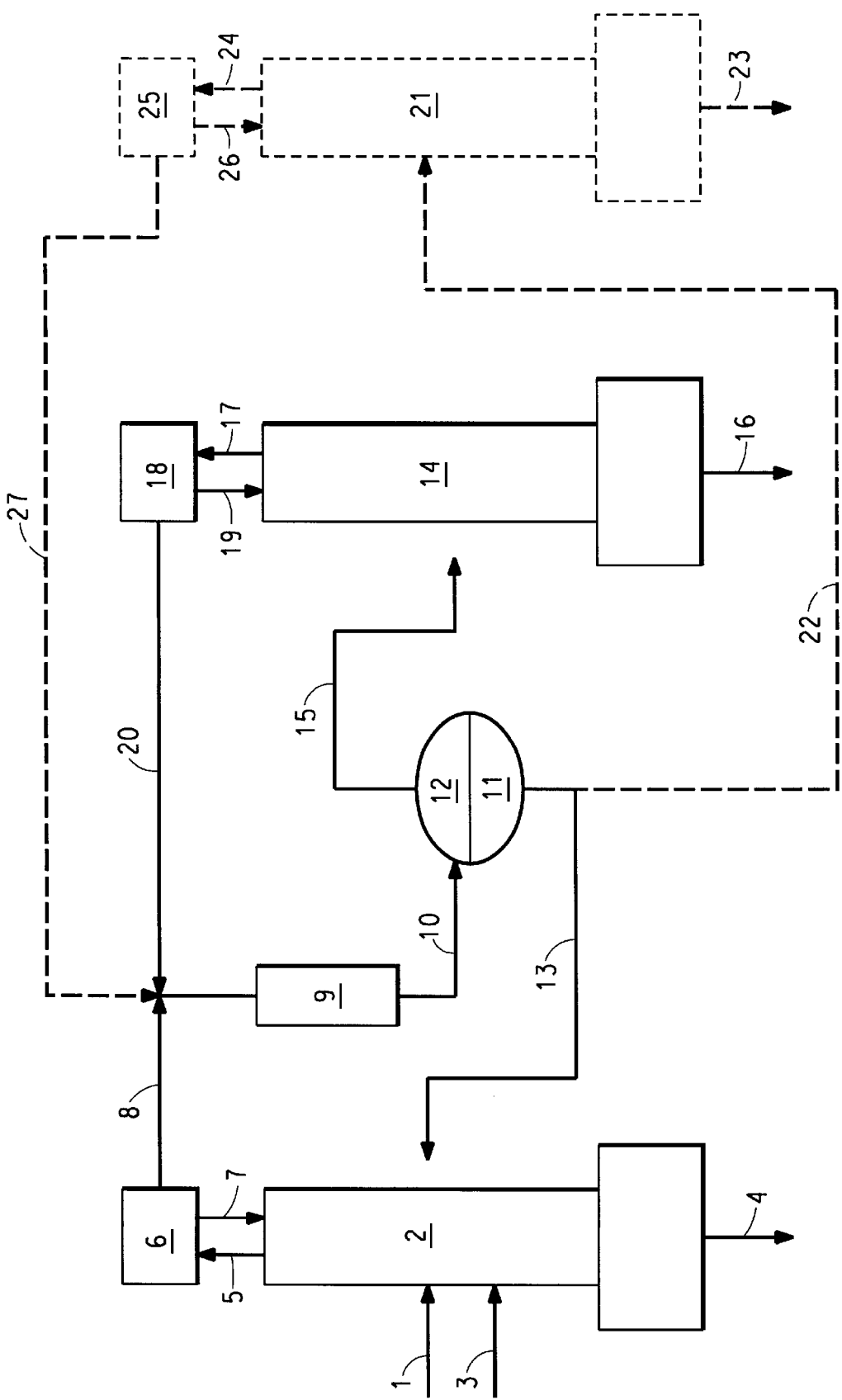
FIG. 1 is a schematic diagram of a distillation system that can be used for practicing an aspect of the inventive process.

The present inventors have found that HFC-245fa may be separated from HF such that either HFC-245fa or HF may be recovered substantially-free of the other, such that high-recovery-efficiency of each is obtained, and such that the separation is effected in an economical manner, by distilling a mixture comprising HF and HFC-245fa in the presence of an entraining agent that interacts in a non-ideal manner with the mixture. The entraining agents of the present invention increase the volatility of HF relative to HFC-245fa thus allowing the HFC-245fa to be separated from HF by distillation.

HFC-245fa and HF in their separated and generally pure states have atmospheric pressure boiling points of about +14° C. and +19° C., respectively. However, a mixture comprising HFC-245fa and HF exhibits non-ideal behavior such that the relative volatility of HFC-245fa to HF becomes 1.0 at specific concentrations of HFC-245fa and HF and specific pressures and temperatures, which indicates the formation of an azeotropic or azeotrope-like composition. The formation of an azeotrope or azeotrope-like composition comprising HF and HFC-245fa makes separation by conventional distillation ineffective in simultaneously recovering HFC-245fa product that is substantially-free of HF and obtaining high-recovery-efficiency of the HFC-245fa product. By conventional distillation is meant that only the relative volatility of the components of the mixture to be separated are used to separate the components.

To determine the relative volatility of HF and HFC-245fa, a method known as the "PTx Method" was used. Use of the PTx Method is described in detail in "Phase Equilibrium in Process Design", Wiley-Interscience Publisher, 1970, written by Harold R. Null, on pages 124 to 126; hereby incorporated by reference. In the PTx method, the total absolute pressure in a cell of known volume is measured at a constant temperature for various known binary compositions of HFC-245fa and HF. These total pressure measurements are converted into equilibrium vapor and liquid compositions in the PTx cell by using an activity coefficient equation model such as the Non-Random, Two-Liquid (NRTL) equation, which represents liquid phase nonidealities. Use of an activity coefficient equation such as the NRTL equation is described in greater detail in "The Properties of Gases and Liquids," $4^{th}$ edition, published by McGraw Hill, written by Reid, Prausnitz and Poling, on pages 241 to 387, and in "Phase Equilibria in Chemical Engineering," published by Butterworth Publishers, 1985, written by Stanley M. Walas, pages 165 to 244. Both aforementioned references are hereby incorporated by reference.

The behavior of HF in such systems may also be calculated by using an appropriate HF association model in conjunction with the aforementioned methods, such as described by W. Schotte, Ind.Eng.Chem.Process Des.Dev. 1980, pp. 432–439; the disclosure of which is hereby incorporated by reference.

Without wishing to be bound by theory, it is believed that the NRTL equation can sufficiently predict whether or not HFC-245fa and HF and/or the following other mixtures behave in an ideal manner, and can sufficiently predict the relative volatilities of the components in such mixtures.

The problems associated with conventional distillation can be solved by the present distillation process using entraining agents. The present process may be employed when the components of the mixture have relative volatilities that are insufficient to permit effective separation of the components by conventional distillation In distillation using entraining agents, an entraining agent is employed which causes the relative volatilities of the components in the starting mixture to be altered such that the relative volatility becomes sufficient to permit separation of the components by distillation. The difficulty in applying this method is that there is no known way of predicting which if any compound will be an effective entraining agent.

The results of PTx measurements and the above calculations indicate that the relative volatilities of HF and HFC-245fa are equal to 1.0 for compositions of HF and HFC-245fa over a range of temperatures. Relative volatilities of 1.0 in a mixture indicate the formation of an azeotrope. The results of PTx measurements and the above calculations indicate that the composition of the azeotropes varies with temperature.

By azeotropic or an azeotrope composition is meant a constant-boiling mixture of two or more substances that behaves as a single substance. One way to characterize an azeotropic composition is that the vapor produced by partial evaporation or distillation of the liquid has the same composition as the liquid from which it is evaporated or distilled, i.e., the mixture distills and refluxes without compositional change. Constant-boiling compositions are characterized as azeotropic because they exhibit either a maximum or minimum boiling point, relative to that of the pure components. Azeotropic compositions are also characterized by a minimum or a maximum in the vapor pressure measurements of the mixture relative to the vapor pressure of the neat components as a function of composition at a constant temperature.

It is also possible to characterize an azeotropic or azeotrope-like composition as a substantially constant-boiling admixture which may appear under many guises, depending upon the conditions chosen, by several criteria:

The composition can be defined as an azeotrope of HF and another compound because the term "azeotrope" is at once both definitive and limitative, and requires effective amounts of HF and the other compound for this unique composition of matter which can be a constant-boiling composition.

It is well known by those skilled in the art, that, at different pressures, the composition of a given azeotrope will vary at least to some degree, as will the boiling point temperature. Thus, an azeotropic or azeotrope-like composition of HF and another compound represents a unique type of relationship but with a variable composition which depends on temperature and/or pressure. Therefore, compositional ranges, rather than fixed compositions, are often used to define azeotropes.

An azeotrope or azeotrope-like composition of HF and another compound can be characterized by defining the compositions as an azeotrope characterized by a boiling point at a given pressure, thus giving identifying characteristics without unduly limiting the scope of the invention by a specific numerical composition, which is limited by and is only accurate as the analytical equipment available.

It is recognized in the art that both the boiling point and the weight (or mole) percentages of each component of the azeotropic composition may change when the azeotrope or azeotrope-like liquid composition is subjected to boiling at different pressures. Thus, an azeotropic or an azeotrope-like composition may be defined in terms of the unique relationship that exists among components or in terms of the exact weight (or mole) percentages of each component of the composition characterized by a fixed boiling point at a specific pressure.

By azeotrope-like is meant a composition that has a constant-boiling characteristic or a tendency not to fractionate upon boiling or evaporation. The composition of the vapor formed is the same as, or substantially the same as, the original liquid composition. During boiling or evaporation, the liquid composition, if it changes at all, changes only to a minimal or negligible extent. An azeotrope-like composition can also be characterized by the area that is adjacent to the maximum or minimum vapor pressure in a plot of composition versus vapor pressure at a given temperature for components in the composition. Herein, a composition is azeotrope-like if, after about 50 weight percent of the composition is removed such as by evaporation or boiling off, the difference between the original composition and the composition remaining is less than about 6 weight %, and normally less than about 3 weight %, relative to the original composition.

It is also recognized in the art that when the relative volatility of the components in a mixture, e.g. HF and at least one other compound, approaches 1.0, such defines the mixture as forming an azeotrope-like composition. When the relative volatility is 1.0, such defines the mixture as forming an azeotrope.

By low-boiling-azeotrope is meant that an azeotropic or azeotrope-like composition boils at a lower temperature at any given pressure than any one of the components that comprise it would separately boil at that pressure. Alternately, by low-boiling azeotrope is meant any azeotropic or azeotrope-like composition that has a higher vapor pressure at any given temperature than the vapor pressure of any one of the components that comprise the azeotrope would separately have at that temperature.

The problems encountered upon conventional distillation of HF/HFC-245fa, such as the need for taller columns, higher energy input, and lower resultant HFC-245fa recovery, can be solved by practicing the present distillation process. This distillation process is used as HF and HFC-245fa have a relative volatility that is insufficient to permit effective separation by conventional distillation.

The present inventors have found that the relative volatility of compositions comprising HF and HFC-245fa can be altered from 1.0 in the presence of entraining agents selected from: hydrocarbons, chlorofluorocarbons, hydrochlorofluorocarbons and fluorocarbons. By entraining agent is meant any agent that, when added to a first mixture, interacts with at least one component in the first mixture to change the relative volatility of the components such that the components may be separated by distillation. Preferably, entraining agents of the present process comprise hydrocarbons, chlorofluorocarbons, hydrochlorofluorocarbons and fluorocarbons having a normal boiling point greater than about −50° C. and less than about 10° C. Preferred entraining agents of the present process are chloro-1,1,1,2-tetrafluoroethane (HCFC-124), chloro-1,1,2,2-tetrafluoroethane (HCFC-124a), dichloro-1,1,2,2-tetrafluoroethane (CFC-114), dichloro-1,1,1,2-tetrafluoroethane (CFC-114a), 1-chloro-1,1-difluoroethane (HCFC-142b), chloropentafluoroethane (CFC-115), and propane.

In one embodiment of the present invention, entraining agent is added to a first mixture comprising HF and HFC-245fa to form a second mixture comprising entraining agent, HF, and HFC-245fa. In the presence of the entraining agent, the relative volatility of the HF and HFC-245fa is increased, with the HF becoming more volatile, thus permitting HF to be removed as a distillation column overhead stream. This second mixture is distilled under conditions such that a third mixture is formed comprising a low-boiling azeotrope comprising entraining agent and HF. By distilling the second mixture under conditions such that a low-boiling HF/entraining agent azeotrope is formed, the HF may be separated from the HFC-245fa by distilling the HF/entraining agent azeotrope third mixture overhead as a distillate stream, and recovering as a distillation column bottoms stream the HFC-245fa that was present in the first mixture, with the HFC-245fa recovered with high-recovery-efficiency and substantially-free of HF.

By substantially-free is meant that the residual HF in the HFC-245fa product is less than 1 parts-per-million-by-weight (ppmw), preferrably less than 100 parts-per-billion-by-weight (ppbw).

By high-recovery-efficiency is meant that greater than 95 weight %, preferably greater than 99 weight % of the HFC-245fa in the initial HFC-245fa-containing mixture is recovered as HFC-245fa substantially-free of HF.

In a further embodiment of the present process, cooling the condensed HF/entraining agent azeotropic or azeotrope-like third mixture results in phase separation of the third mixture into two liquid phases. One of these phases is HF-enriched and the other phase is entraining agent-enriched, both enriched relative to the HF and entraining agent concentrations in the third mixture. The entraining agent-enriched layer obtained from this cooling step may be fed back to the distillation step carried out on the second mixture without further processing, or it can optionally be distilled under conditions such that any HF remaining in the entraining agent-enriched phase forms a low-boiling azeotropic or azeotrope-like composition with the entraining agent, where the HF/entraining agent azeotropic or azeotrope-like composition is distilled overhead leaving an entraining agent product substantially-free of HF to exit the column bottoms. This HF/entraining agent distillate may optionally be further separated by again feeding it to the aforementioned cooling step.

The HF-enriched layer from the cooling step may be used without further processing or, where further separation and purification of either the BF or entraining agent is desirable, it may optionally be distilled under conditions that form a low-boiling HF/entraining agent azeotropic or azeotrope-like composition, recovering the HF/entraining agent azeotropic or azeotrope-like composition overhead as distillate, and recovering HF substantially-free of entraining agent from the column bottoms. The HF obtained from this step may be recycled back to a reaction step to produce the HFC-245fa or used for other purposes. The HF/entraining agent azeotropic of azeotrope-like composition distillate may be further separated by again feeding it to the cooling step.

The present invention thus comprises a process for separating HF from HFC-245fa comprising the steps of:

(1) contacting a first mixture comprising 1,1,1,3,3-pentafluoropropane (HFC-245fa) and hydrogen fluoride (HF) with an effective amount of entraining agent selected from the group consisting of hydrocarbons, chlorofluorocarbons, and hydrochlorofluorocarbons to form a second mixture, (2) distilling the second mixture and thereby separating the 1,1,1,3,3-pentafluoropropane (HC-245fa) from hydrogen fluoride (HF) and entraining agent, (3) recovering 1,1,1,3,3-pentafluoropropane (HFC-245fa) as a distillation column bottom stream, (4) recovering an azeotropic or azeotrope-like third mixture comprising HF and entraining agent as a distillation column overhead stream from said distilling step, (5) optionally cooling and thereby phase-separating the condensed third mixture into a fourth mixture comprising an HF-enriched phase and a fifth mixture comprising an entraining agent enriched phase, (6) optionally distilling the fourth and/or fifth mixtures under conditions sufficient to form an azeotrope or azeotrope-like sixth mixture comprising HF and entraining agent as distillation column overhead stream (7) optionally recovering a seventh mixture comprising HF or entraining agent as a distillation column bottom stream from said distilling step of the fourth and/or fifth mixtures, (8) optionally recycling the sixth mixture to said cooling step, and (9) optionally recycling the seventh mixture to said distilling step of the fourth and/or fifth mixtures.

By effective amount of entraining agent is meant an amount of at least one entraining agent, which in the presence of HF and HFC-245fa, either results in the formation of a lower-boiling azeotropic or azeotrope-like composition comprising HF and entraining agent or otherwise causes the volatility of the HF to increase relative to the HFC-245fa. This definition includes amounts of each component which may vary depending on the pressure applied to the composition so long as the azeotrope or azeotrope-like compositions continue to exist at the different pressures, but with possible different boiling point temperatures. Effective amount also includes the amounts, such as may be expressed in weight percentages or mole percentages, of each component of the compositions of the instant invention which form azeotropic or azeotrope-like compositions at temperature or pressures other than as described herein. An effective amount of the entraining agent depends upon the ratio of the HF to the entraining agent in the HF/entraining agent azeotrope thus formed. Useful in the present process are compositions of effective amounts of HFC-245fa and HF, HCFC-124 and HF, HCFC-124a and HF, HCFC-142b and HF, CFC-114 and HF, CFC-114a and HF, CFC-115 and HF, and propane and HF such that after about 50 weight % of an original composition is evaporated or boiled off to produce the remaining composition, the difference between the original composition and the remaining composition is typically about 6 weight percent or less, and normally 3 weight percent or less.

The entraining agents used in the present invention are generally commercially available. If desired, the entraining agents may be subsequently removed from the HF by a variety of methods. A preferred method is to condense and cool the distillate from the first distillation comprising the HF/entraining agent azeotrope. With condensing and cooling the HF/entraining agent distillate, the mixture separates into two liquid layers, one HF-rich relative to the HF/entraining agent azeotrope composition, the other entraining agent-rich relative to the azeotrope composition.

The entraining agent-rich layer may then be recycled to the HFC-245fa/HF separation column for reuse, or if a stream substantially free of HF or complete separation of the HF is desired, this organic phase may be fed to a distillation column operated at a pressure and temperature that causes an azeotropic or azeotrope-like composition to form, composed of HF and the entraining agent. Since the entraining agent is now in excess of the azeotropic composition, the HF may be removed from that excess entraining agent by distilling the HF/entraining agent azeotrope overhead, with entraining agent substantially free of HF removed as bottoms from the column. By recycling the HF/entraining agent azeotrope distilled overhead from this column back to the decanter, essentially all of the entraining agent may be recovered as entraining agent substantially free of HF.

Similarly, the HF-rich layer from the cooling/decantation step may then be recycled back to the reaction step, or, if a HF stream substantially free of entraining agent is desired, this HF phase may be fed to a distillation column operated at a pressure and temperature that causes an azeotropic or azeotrope-like composition to form comprising HF and the entraining agent. Since the HF is now in excess of the azeotropic composition, the entraining agent may be removed from that excess HF by distilling the HF/entraining agent azeotrope overhead, with HF substantially free of organic removed as bottoms from the column. By recycling the HF/organic azeotrope overhead from this column back to the cooler/decanter, essentially all of the HF may be recovered as pure product.

The specific conditions that can be used for practicing the invention depend upon a number of interrelated design parameters such as the diameter of the column, selected feed points, the number of separation stages in the column, among other parameters. The temperature and heat transfer area of the overhead condenser is normally sufficient to substantially fully condense the overhead product, or is optionally sufficient to achieve the desired reflux ratio by partial condensation.

The temperature that is employed at a given step in the inventive process is a function of the pressure and design characteristics of the distillation column, e.g., the ratio of entraining agent to the first mixture.

Certain aspects of the invention can be better understood by reference to FIG. 1. FIG. 1 schematically illustrates a system which can be used to perform one aspect of the inventive distillation process. A first mixture comprising HFC-245fa and HF is supplied via conduit 1 to distillation column 2. At least one liquid entraining agent is supplied via conduit 3 to distillation column 2. The entraining agent may alternately be mixed in with the HFC-245fa and HF containing mixture prior to the distillation column and simultaneously fed in via conduit 1. Material comprising HFC-245fa substantially free of HF is removed from the column 1 bottoms via conduit 4. Material comprising the Entraining Agent and HF is removed from the column 2 as distillate via conduit 5 and transported to condenser 6. A fraction of the distillate is then returned to column 2 as reflux via conduit 7, while the remainder is transported via conduit 8 to cooler 9 and from there to the decanter 10. The material entering the decanter separates into two liquid layers, one liquid layer entraining agent-rich layer, e.g., 11, the other liquid layer HF-rich, e.g., 12 on the top. The entraining agent-rich layer is transported back to column 2 via conduit 13. The HF-rich layer is transported to column 14 via conduit 15. Material comprising HF substantially free of entraining agent is removed from column 14 via conduit 16. Material comprising the entraining agent and HF is removed from the column 14 as distillate via conduit 17 and transported to condenser 18. A fraction of the distillate is then returned to column 14 as reflux via conduit 19, while the remainder is transported via conduit 20 to mix with the material in conduit 8 prior to its entry into cooler 9. The entraining agent-rich layer, e.g., 11, in the decanter typically still contains concentrations of HF possibly as high as several weight %. Optionally, instead of being sent immediately back to column 2 via conduit 13, the entraining agent-rich liquid layer, e.g., 11, in the decanter can instead first be transported to distillation column 21 via conduit 22. Material comprising the entraining agent substantially-free of HF is removed from the column 21 bottoms via conduit 23. A mixture comprising the entraining agent and HF is removed from column 21 via conduit 24 and transported to condenser 25. A fraction of the distillate is then returned to column 21 as reflux via conduit 26, while the remainder is transported via conduit 27 to mix with the material in conduit 8 prior to its entry into cooler 9.

Figure 2:
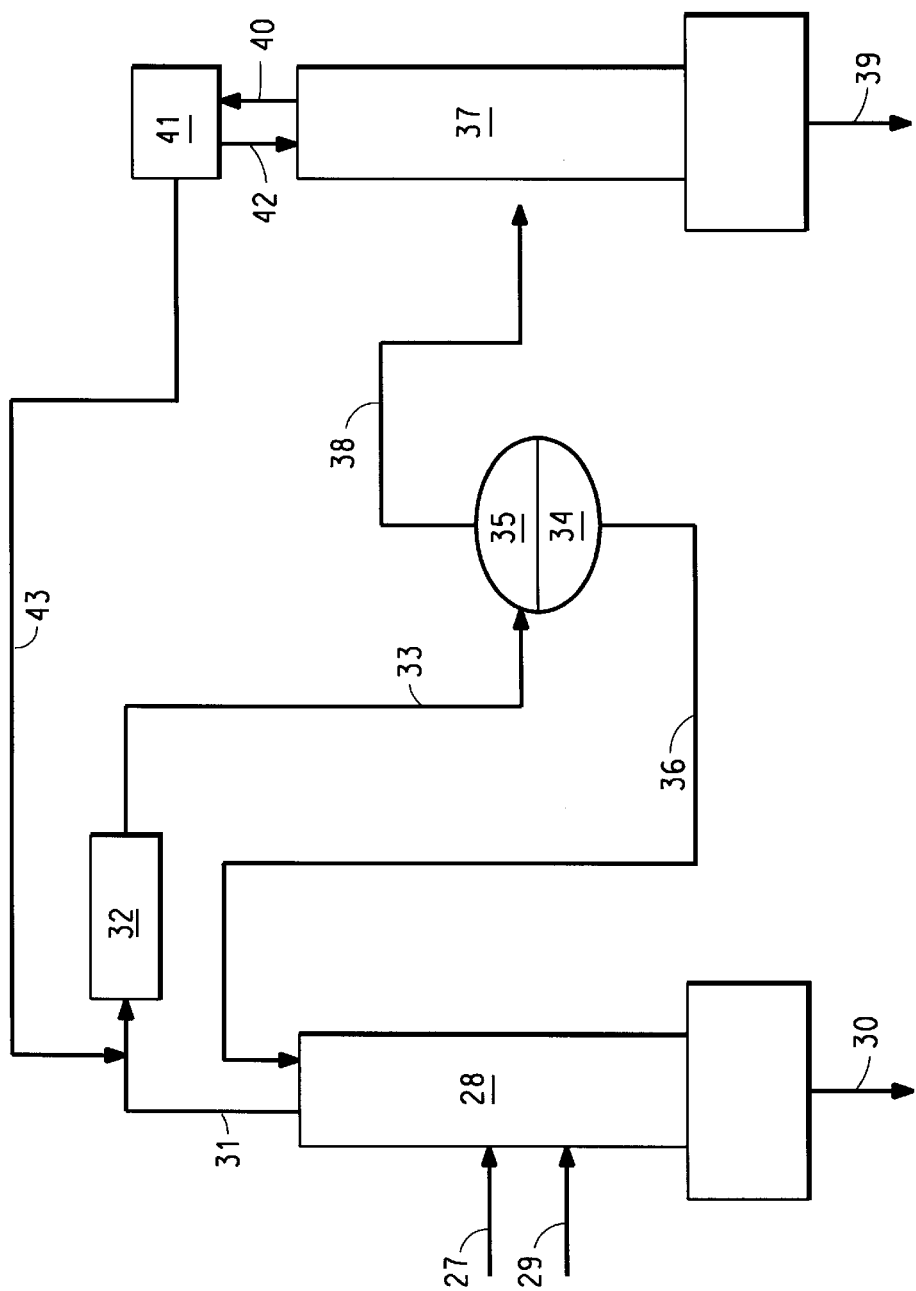
FIG. 2 is a schematic diagram of a distillation system that can be used for practicing an aspect of the inventive process.

FIG. 2 schematically illustrates a system which can be used to perform another aspect of the inventive distillation process. A first mixture comprising HFC-245fa and HF is supplied via conduit 27 to distillation column 28. At least one liquid entraining agent is supplied via conduit 29 to distillation column 28. The entraining agent may alternately be mixed in with the mixture comprising HFC-245fa and HF prior to the distillation column and simultaneously fed in via conduit 27. Material comprising HFC-245fa substantially-free of HF is removed from the column 28 bottoms via conduit 30. Material comprising entraining agent and HF is removed from the column 28 as distillate via conduit 31 and transported to coolers, and from there to the decanter 33. The material entering the decanter separates into two liquid layers, one layer entraining agent-rich, e.g., 34, the other layer HF-rich, e.g., 35. The entraining agent-enriched layer is transported back to column 28 as reflux via conduit 36. The HF-enriched layer is transported to column 37 via conduit 38. Material comprising HF substantially-free of entraining agent is removed from column 37 via conduit 39. Material comprising the entraining agent and HF is removed from the column 37 as distillate via conduit 40 and transported to condenser 41. A fraction of the distillate is then returned to column 37 as reflux via conduit 42, while the remainder is transported via conduit 43 to mix with the material in conduit 31 prior to its entry into cooler 32. In contrast to the configuration shown in FIG. 1, the configuration shown in FIG. 2 allows for significantly improved energy efficiency and reduced equipment costs.

EXAMPLES

The following Examples are provided to illustrate certain aspects of the present invention, and do not intend to limit the scope of the instant invention. The following Examples employ the NRTL interaction parameters identified earlier. In the following examples, each stage is based upon a 100% operational or performance efficiency. Differing column designs and operating conditions are employed using different entraining agents in order to maximize the performance of each distillation. The total stages include the condenser and reboiler, with the condenser counted as stage No. 1.

Example 1

Figure 3:
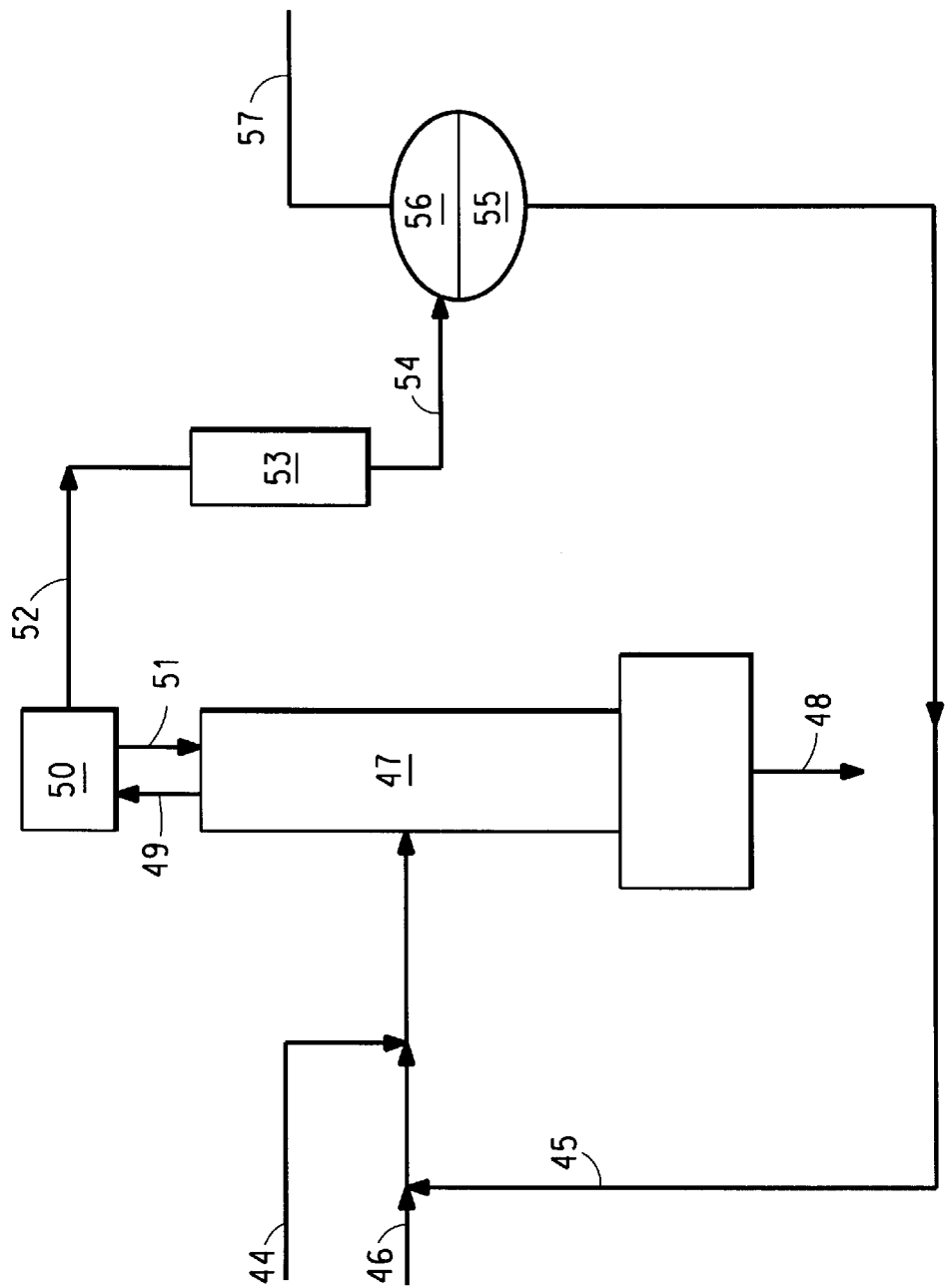
FIG. 3 is a schematic diagram of a distillation system that can be used for practicing an aspect of the inventive process.

In this Example, a feed stream consisting of 75 mole % HF and 25 mole % HFC-245fa is fed to a distillation column at a rate of 100 lbs. per hour by way of conduit 44 as shown in FIG. 3. Either CFC-115, HCFC-124, HCFC-142b, CFC-114, or propane is added to this feed stream as the entraining agent prior to its entry into the distillation column, with the flowrate shown being the total amount of each entrainer being fed to the column. The entraining agent is added to column 47 by recycling the decanter's organic-rich phase 55 via conduit 45 plus supplemental entraining agent added via conduit 46. Product HFC-245fa is removed as the column bottoms via conduit 48. Distillate from column 47 is sent via conduit 49 to the column condenser 50, where it is condensed and part of the condensate recycled as reflux via conduit 51. The remaining condensed distillate is fed via conduit 52 through cooler 53 where it is cooled down to a decanter temperature of −20° C., then is fed to a decanter 54 in which it separates into two liquid layers. The decanter's lower organic-rich liquid layer, 55 is then fed back via conduit 45 and mixed with the HF and HFC-245fa feed stream and again distilled. The decanters upper HF-rich liquid layer, 56, may be processed by methods previously disclosed in this specification.

TABLE 1

| Entraining Agent | CFC-115 | HCFC-124 | HCFC-142b | CFC-114 | Propane |
|---|---|---|---|---|---|
| # of stages | 45 | 40 | 50 | 55 | 55 |
| HFC-245fa Feed Stage | 12 | 15 | 12 | 35 | 20 |
| Entraining Agent Feed Stage | 12 | 15 | 12 | 35 | 20 |
| Column Top Temperature (° C.) | −12.24 | 14.41 | 11.75 | 22.32 | 0.47 |
| Reflux Temperature (° C.) | −12.54 | 12.50 | 10.10 | 21.79 | −14.59 |
| Distillate Temperature (° C.) | −12.54 | 12.50 | 10.10 | 21.79 | −14.59 |
| Base Temperature (° C.) | 48.64 | 48.64 | 41.22 | 48.64 | 48.64 |
| HFC-245fa/HF Feed Temperature (° C.) | 20.00 | 20.00 | 20.00 | 20.00 | 20.00 |
| Entraining Agent Feed Temperature (° C.) | 20.00 | 20.00 | 20.00 | 20.00 | 20.00 |
| Top Pressure (psia) | 44.8 | 44.8 | 34.8 | 44.8 | 44.8 |
| Condenser Pressure (psia) | 44.7 | 44.7 | 34.7 | 44.7 | 44.7 |
| Base Pressure (psia) | 47.7 | 47.7 | 37.7 | 47.7 | 47.7 |
| Crude HFC-245fa Feed Rate (lbs/hr) | 100.0 | 100.0 | 100.0 | 100.0 | 100.0 |
| Entraining Agent Feed Rate (lbs/hr) | 200.0 | 100.0 | 100.0 | 21.0 | 20.0 |
| Distillate Rate (lbs/hr) | 204.9 | 105.0 | 105.1 | 33.0 | 38.6 |
| Bottoms Rate (lbs/hr) | 95.1 | 95.0 | 94.9 | 88.0 | 81.4 |
| Reflux Rate (lbs/hr) | 500 | 400 | 500 | 500 | 500 |
| Reflux Ratio (molar) | 2.44 | 3.81 | 4.76 | 15.16 | 12.95 |
| Condenser Duty (PCU/hr) | −20671 | −22214 | −34409 | −23669 | 44898 |
| Reboiler Duty (PCU/hr) | 14813 | 22810 | 29905 | 24449 | 43213 |
| HFC-245/HF Feed | | | | | |

TABLE 1-continued

| Entraining Agent | CFC-115 | HCFC-124 | HCFC-142b | CFC-114 | Propane |
|---|---|---|---|---|---|
| HFC-245fa (lb-mol/hr) | 0.7106 | 0.7106 | 0.7106 | 0.7106 | 0.7106 |
| HF (lb-mol/hr) | 0.2369 | 0.2369 | 0.2369 | 0.2369 | 0.2369 |
| Total (lb-mol/br) Distillate | 0.9475 | 0.9475 | 0.9475 | 0.9475 | 0.9475 |
| HFC-245fa (lb-mol/hr) | 0.0015 | 0.0019 | 0.0025 | 0.0540 | 0.1036 |
| HF (lb-mol/br) | 0.2369 | 0.2369 | 0.2369 | 0.2369 | 0.2369 |
| Entraining Agent (lb-mol/hr) | 1.2947 | 0.7327 | 0.9950 | 0.1229 | 0.4536 |
| Total (lb-mol/hr) | 1.5331 | 0.9715 | 1.2344 | 0.4137 | 0.7940 |
| HFC-245fa Overhead (lb/br) | 0.2053 | 0.2599 | 0.3303 | 7.2335 | 13.8836 |
| HFC-245fa Lost in Overhead (%) Tails | 0.2155 | 0.2729 | 0.3467 | 7.5933 | 14.5743 |
| HFC-245fa (lb-mol/hr) | 0.7091 | 0.7087 | 0.7082 | 0.6567 | 0.6070 |
| HF (lb-mol/hr) | 0.0000 | 0.0000 | 0.0000 | 0.0000 | 0.0000 |
| Entraining Agent (lb-mol/hr) | 0.0000 | 0.0000 | 0.0000 | 0.0000 | 0.0000 |
| Total (lb-mol/hr) | 0.7091 | 0.7087 | 0.7082 | 0.6567 | 0.6070 |
| HF (ppm-molar) | 0.0000 | 0.0000 | 0.0000 | 0.0000 | 0.0000 |
| Entraining Agent (ppm-molar) | 0.0000 | 0.0044 | 0.0000 | 0.0006 | 0.0000 |
| HFC-245fa (mol %) | 100.00000 | 100.00000 | 100.00000 | 100.00000 | 100.00000 |

Example 2

This Example demonstrates the existence of azeotropic of azeotrope-like compositions between the binary pair mixtures consisting essentially of HF and HFC-245fa; HF and HCFC-124; HF and CFC-114; HF and CFC-114a; HF and CFC-115; HF and HCFC-142b. To determine the relative volatility of each binary pair, the so-called PTx Method was used. In this procedure, for each binary, the total absolute pressure in a PTx cell of known volume was measured at a constant temperature for various known compositions. These measurements were then reduced to equilibrium vapor and liquid compositions using the NRTL equation. Samples of selected vapor and liquid sets were obtained and analyzed to verify their respective compositions.

The vapor pressure measured versus the composition in the PTx cell for the HF and HFC-245fa; HF and HCFC-124; HF and CFC-114; HF and CFC-114a; HF and CFC-115; HF and HCFC-142b systems are shown in FIGS. 4 through 9, respectively. The experimental data points are shown on each Figure as solid points, and the curve is then fitted from that data.

Figure 4:
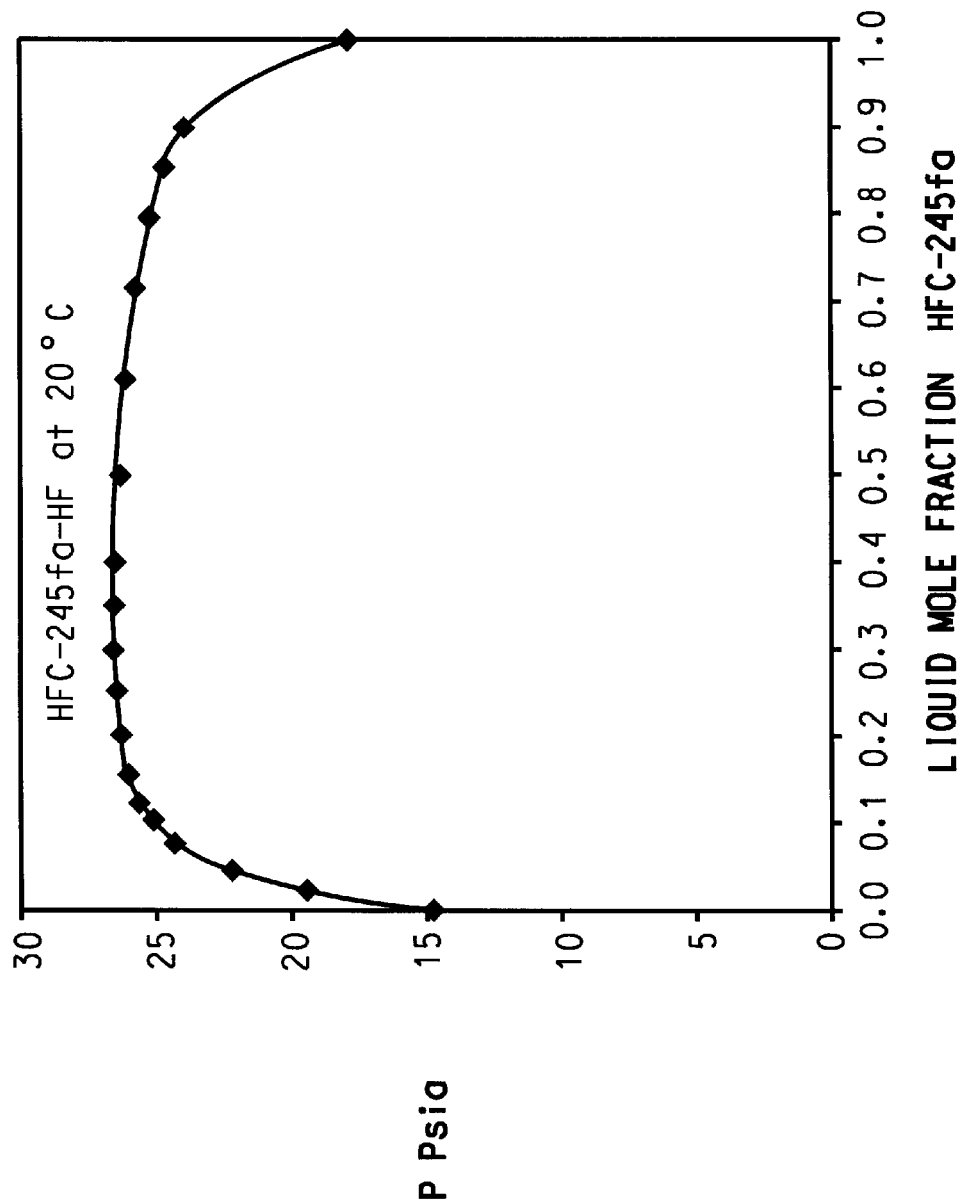
FIG. 4 is a graphical representation at +20° C. of an azeotropic and azeotrope-like composition formed between HF and HFC-245fa.

Referring now to FIG. 4, FIG. 4 illustrates graphically the formation of an azeotropic or azeotrope-like composition consisting essentially of HF and HFC-245fa at a temperature of about 20° C., as indicated by mixtures of HF and HFC-245fa having a higher vapor pressure than either pure component. This system exhibits a maximum or peak vapor pressure at a temperature of +20° C. of about 26.7 psia, and contains about 66.1 mole percent HF and 33.9 mole percent HFC-245fa in the vapor space of this higher pressure region. Based upon these findings, it has been calculated that an azeotropic or azeotrope-like composition of about 84.4 mole percent HF and 15.6 mole percent HFC-245fa is formed at a temperature of about −50° C. and 0.8 psia. Based upon these findings, it has been calculated that an azeotropic or azeotrope-like composition of about 44.1 mole percent HF and 55.9 mole HFC-245fa is formed at a temperature of about +130° C. and 559 psia. Accordingly, the present invention provides an azeotropic of azeotrope-like composition consisting essentially of from about 84.4 to 44.1 mole % HF and from 15.6 to 55.9 mole % HFC-245fa, said composition having a boiling point from about −50° C. at 0.80 psia to about +130° C. at 559 psia.

Figure 5:
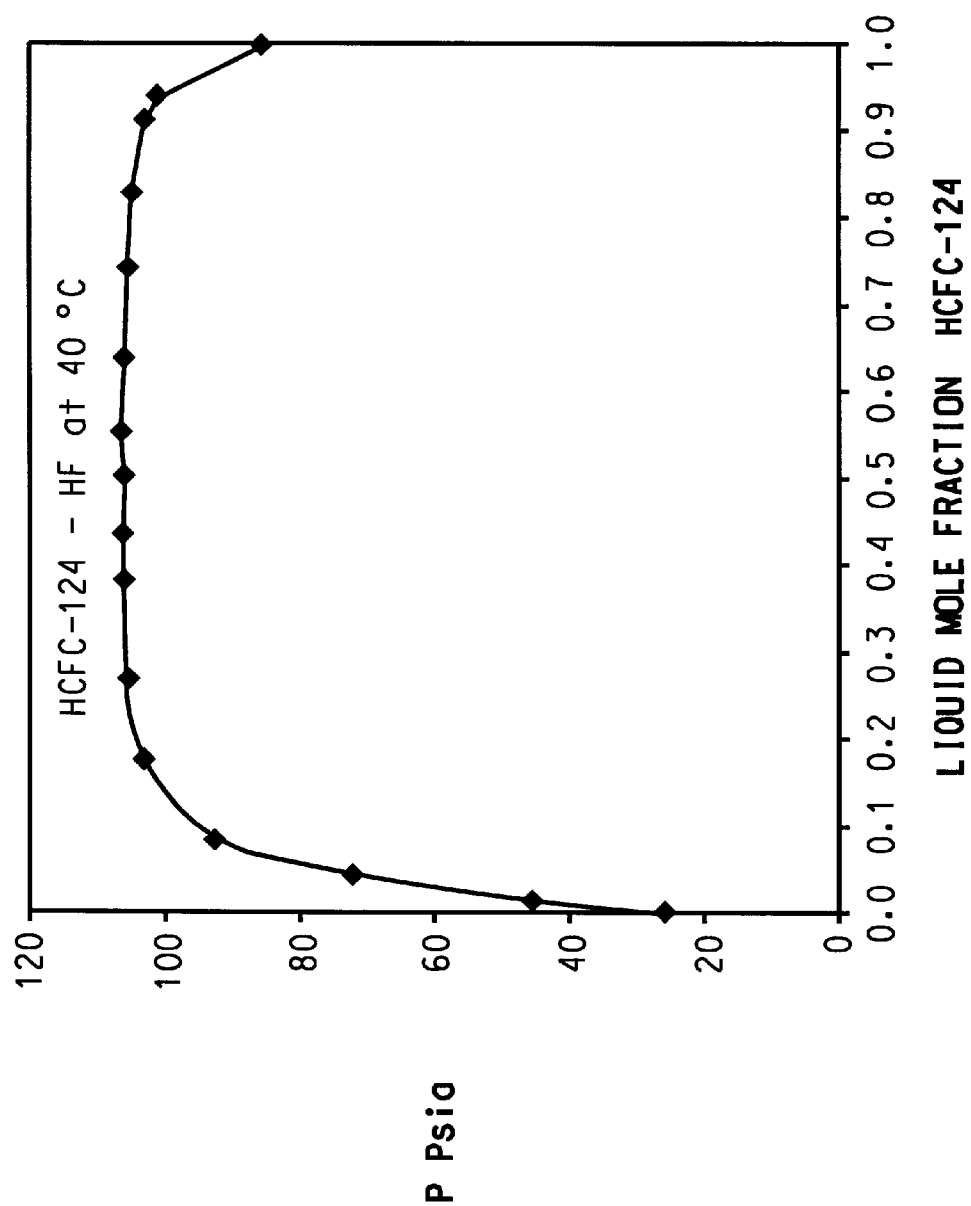
FIG. 5 is a graphical representation at +40° C. of an azeotropic and azeotrope-like composition formed between HF and HCFC-124.

Referring now to FIG. 5, FIG. 5 illustrates graphically the formation of an azeotropic or azeotrope-like composition consisting essentially of HF and HCFC-124 at a temperature of about 40° C., as indicated by mixtures of HF and HCFC-124 having a higher vapor pressure than either pure component at that temperature This system exhibits a maximum or peak pressure at +40° C. of about 107 psia, and contains about 36 mole percent HF and 64 mole percent HCFC-124 in the vapor space of this higher pressure region. Accordingly, the present invention provides an azeotropic or azeotrope-like composition consisting essentially of about 36 mole percent HF and 64 mole percent HCFC-124, having a boiling point of about +40° C. at 107 psia. Based upon these findings, it has been calculated that an azeotropic or azeotrope-like composition of about 42 mole percent HF and 58 mole percent HCFC-124 is formed at a temperature of about −17° C. and 13.9 psia. Based upon these findings, it has been calculated that an azeotropic or azeotrope-like composition of about 39.0 mole percent HF and 61.0 mole HCFC-124 is formed at a temperature of about +120° C. and 1130 psia. Accordingly, the present invention provides an azeotropic of azeotrope-like composition consisting essentially of from about 42 to 39 mole % HF and from 58 to 61 mole % HCFC-124, said composition having a boiling point from about −17° C. at 13.9 psia to about +120° C. at 1130 psia.

Figure 6:
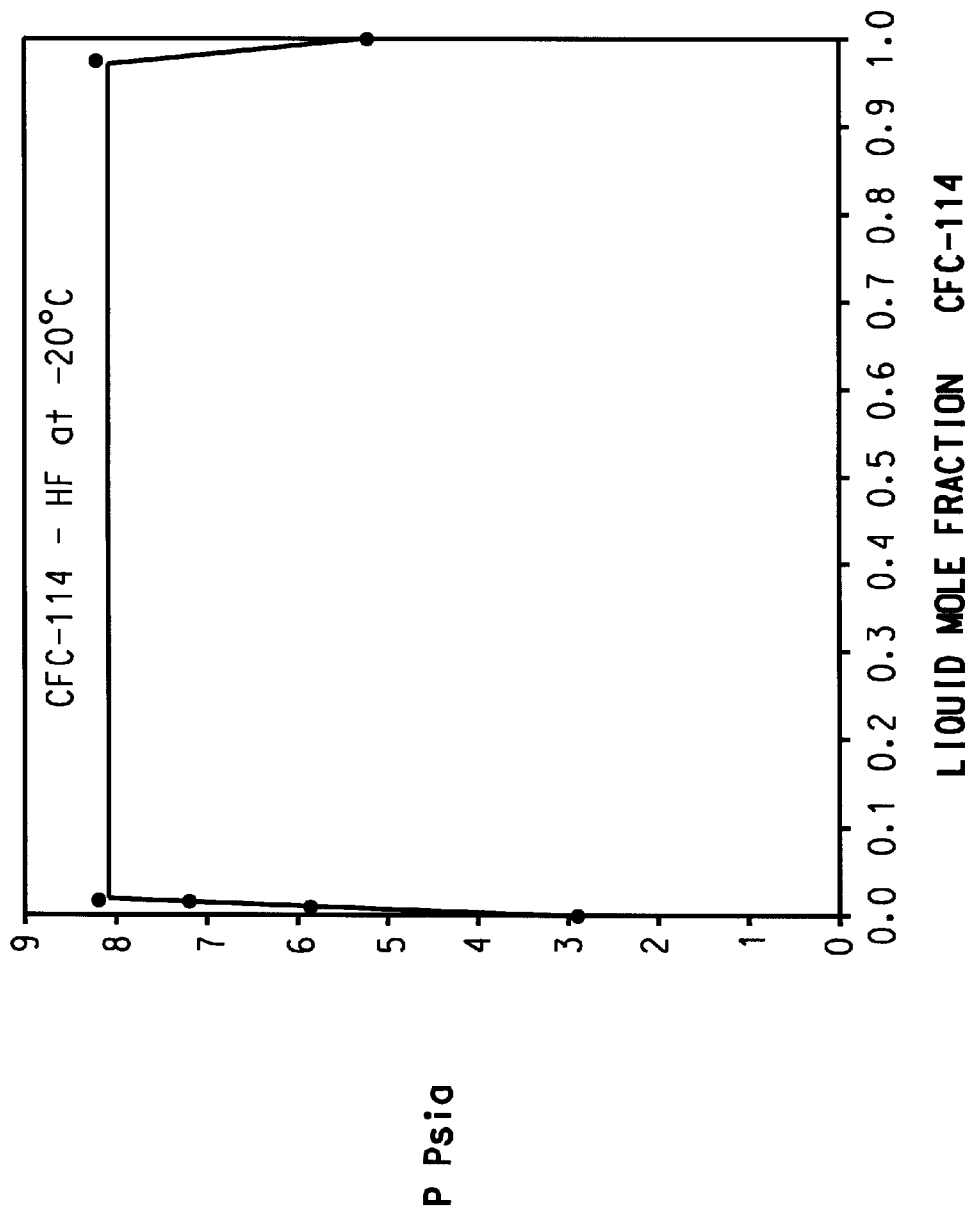
FIG. 6 is a graphical representation at about −20° C. of an azeotropic and azeotrope-like composition formed between HF and CFC-114.

Referring now to FIG. 6, FIG. 6 illustrates graphically the formation of an azeotropic or azeotrope-like composition consisting essentially of HF and CFC-114 at a temperature of about −20° C., as indicated by mixtures of HF and CFC-114 having a higher vapor pressure than either pure component at that temperature This system exhibits a maximum or peak pressure at −20° C. of about 8.2 psia, and contains about 67 mole percent HF and 33 mole percent CFC-114 in the vapor space of this higher pressure region. Accordingly, the present invention provides an azeotropic or azeotrope-like composition consisting essentially of about 67 mole percent HF and 33 mole percent HCFC-124, having a boiling point of about −20° C. at 8.2 psia. Based upon these findings, it has been calculated that an azeotropic or azeotrope-like composition of about 68 mole percent HF and 32 mole percent CFC-1 14 is formed at a temperature of about −50° C. and 1.6 psia Based upon these findings, it has been calculated that an azeotropic or azeotrope-like composition of about 50 mole percent HF and 50 mole CFC-114 is formed at a temperature of about +100° C. and 427 psia. Accordingly, the present invention provides an azeotropic of azeotrope-like composition consisting essentially of from about 68 to 50 mole % HF and from 32 to 50 mole % CFC-114, said composition having a boiling point from about −50° C. at 1.6 psia to about +100° C. at 427 psia.

Figure 7:
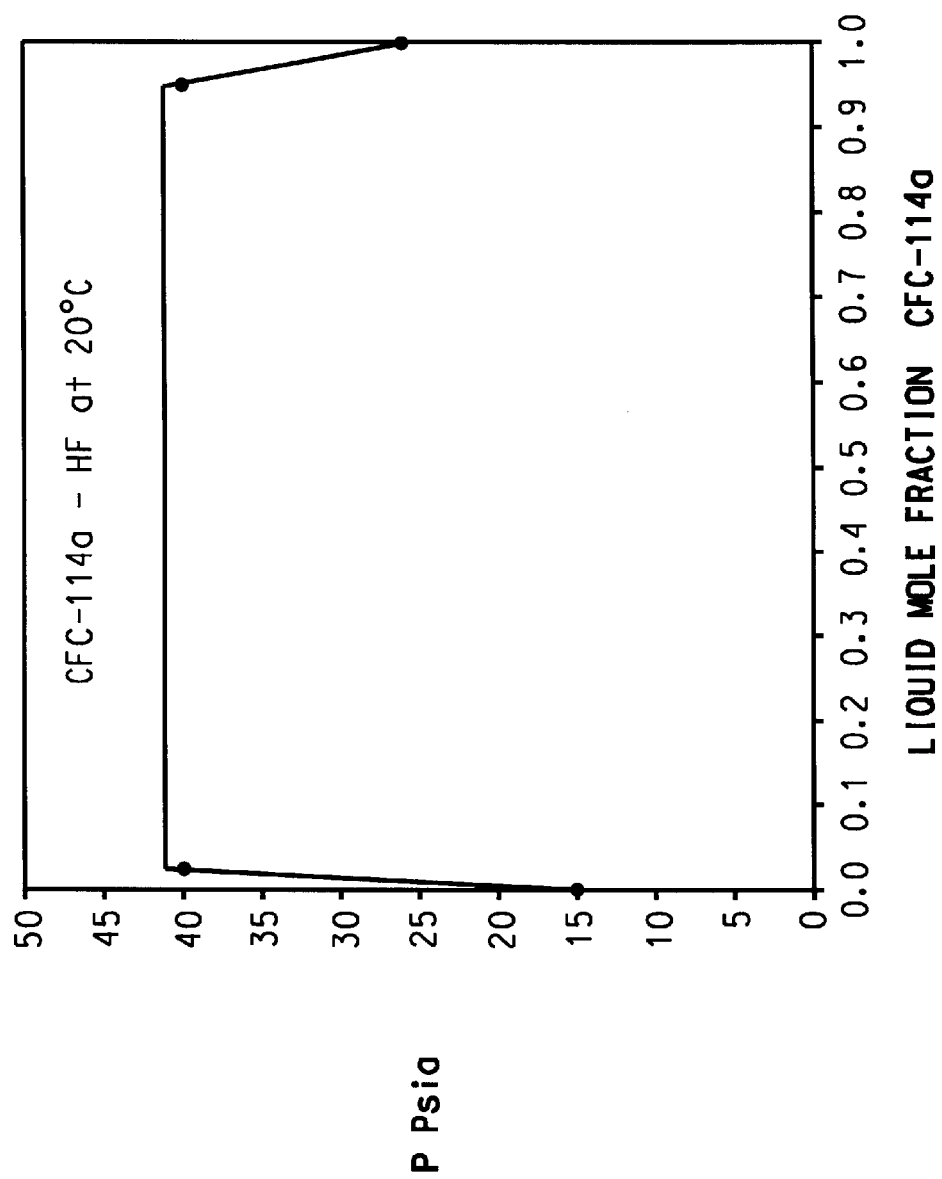

Referring now to FIG. 7, FIG. 7 illustrates graphically the formation of an azeotropic or azeotrope-like composition consisting essentially of HF and CFC-114a at a temperature of about +20° C., as indicated by mixtures of HF and CFC-114a having a higher vapor pressure than either pure component at that temperature This system exhibits a maximum or peak pressure at +20° C. of about 42 psia, and contains about 64 mole percent HF and 37 mole percent CFC-114 in the vapor space of this higher pressure region. Accordingly, the present invention provides an azeotropic or azeotrope-like composition consisting essentially of about 63 mole percent HF and 37 mole percent HCFC-124, having a boiling point of about +20° C. at 42 psia Based upon these findings, it has been calculated that an azeotropic or azeotrope-like composition of about 65 mole percent HF and 35 mole percent CFC-114a is formed at a temperature of about −25° C. and 16.8 psia. Based upon these findings, it has been calculated that an azeotropic or azeotrope-like composition of about 57 mole percent HF and 43 mole CFC-114a is formed at a temperature of about +100° C. and 365 psia. Accordingly, the present invention provides an azeotropic of azeotrope-like composition consisting essentially of from about 65 to 57 mole % HF and from 35 to 43 mole % CFC-114a, said composition having a boiling point from about −25° C. at 16.8 psia to about +100° C. at 365 psia.

Figure 8:
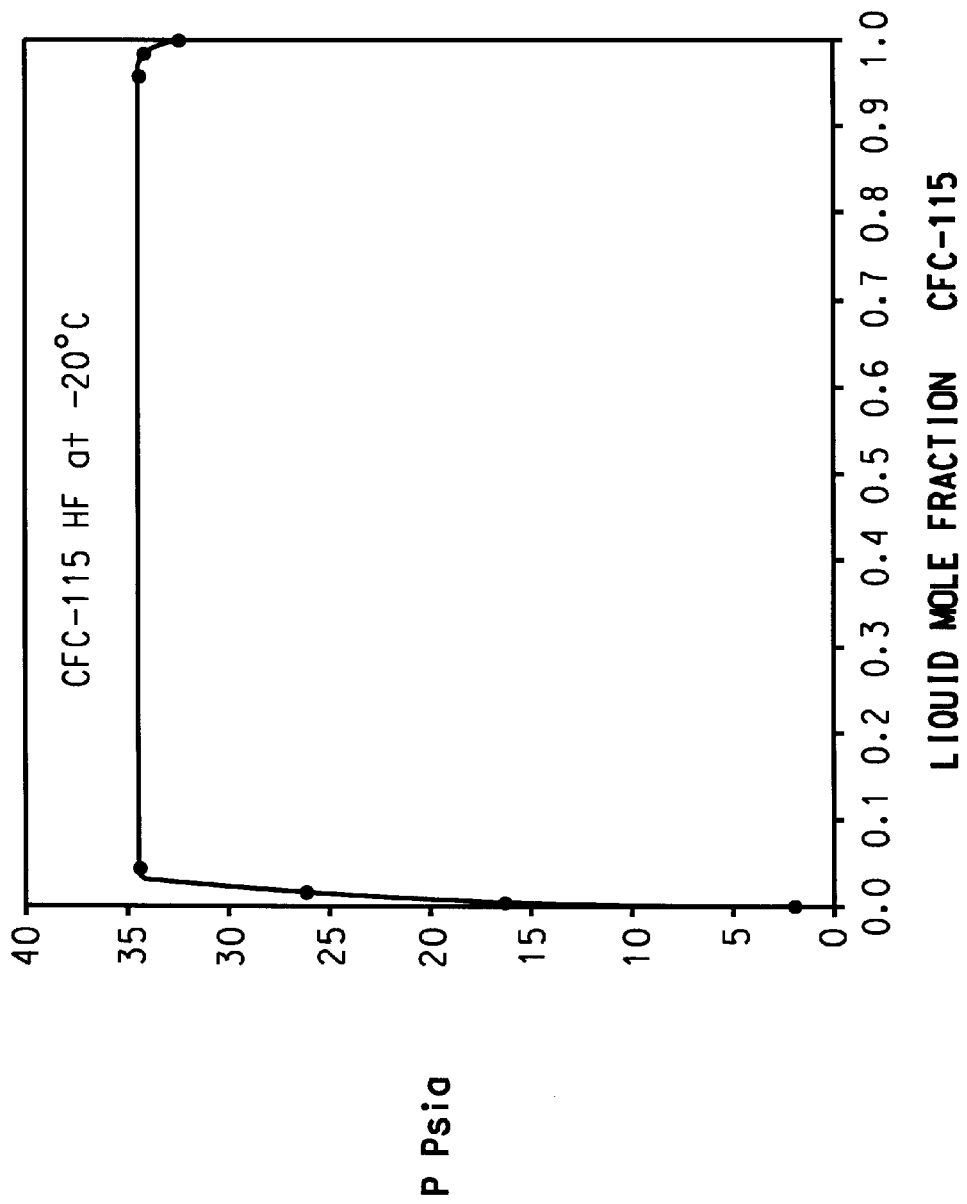
FIG. 8 is a graphical representation at about −20° C. of an azeotropic and azeotrope-like composition formed between HF and CFC-115.

Referring now to FIG. 8, FIG. 8 illustrates graphically the formation of an azeotropic or azeotrope-like composition consisting essentially of HF and CFC-115 at a temperature of about −20° C., as indicated by mixtures of HF and CFC-115 having a higher vapor pressure than either pure component at that temperature This system exhibits a maximum or peak pressure at −20° C. of about 35 psia, and contains about 25 mole percent HF and 75 mole percent CFC-114 in the vapor space of this higher pressure region. Accordingly, the present invention provides an azeotropic or azeotrope-like composition consisting essentially of about 25 mole percent HF and 75 mole percent CFC-115, having a boiling point of about −20° C. at 35 psiaBased upon these findings, it has been calculated that an azeotropic or azeotrope-like composition of about 17 mole percent HF and 83 mole percent CFC-115 is formed at a temperature of about −60° C. and 5.5 psia. Based upon these findings, it has been calculated that an azeotropic or azeotrope-like composition of about 24 mole percent HF and 76 mole % CFC-115 is formed at a temperature of about +50° C. and 287 psia. Accordingly, the present invention provides an azeotropic of azeotrope-like composition consisting essentially of from about 17 to 24 mole % HF and from 83 to 76 mole % CFC-115, said composition having a boiling point from about 60° C. at 5.5 psia to about +50° C. at 287 psia.

Figure 9:
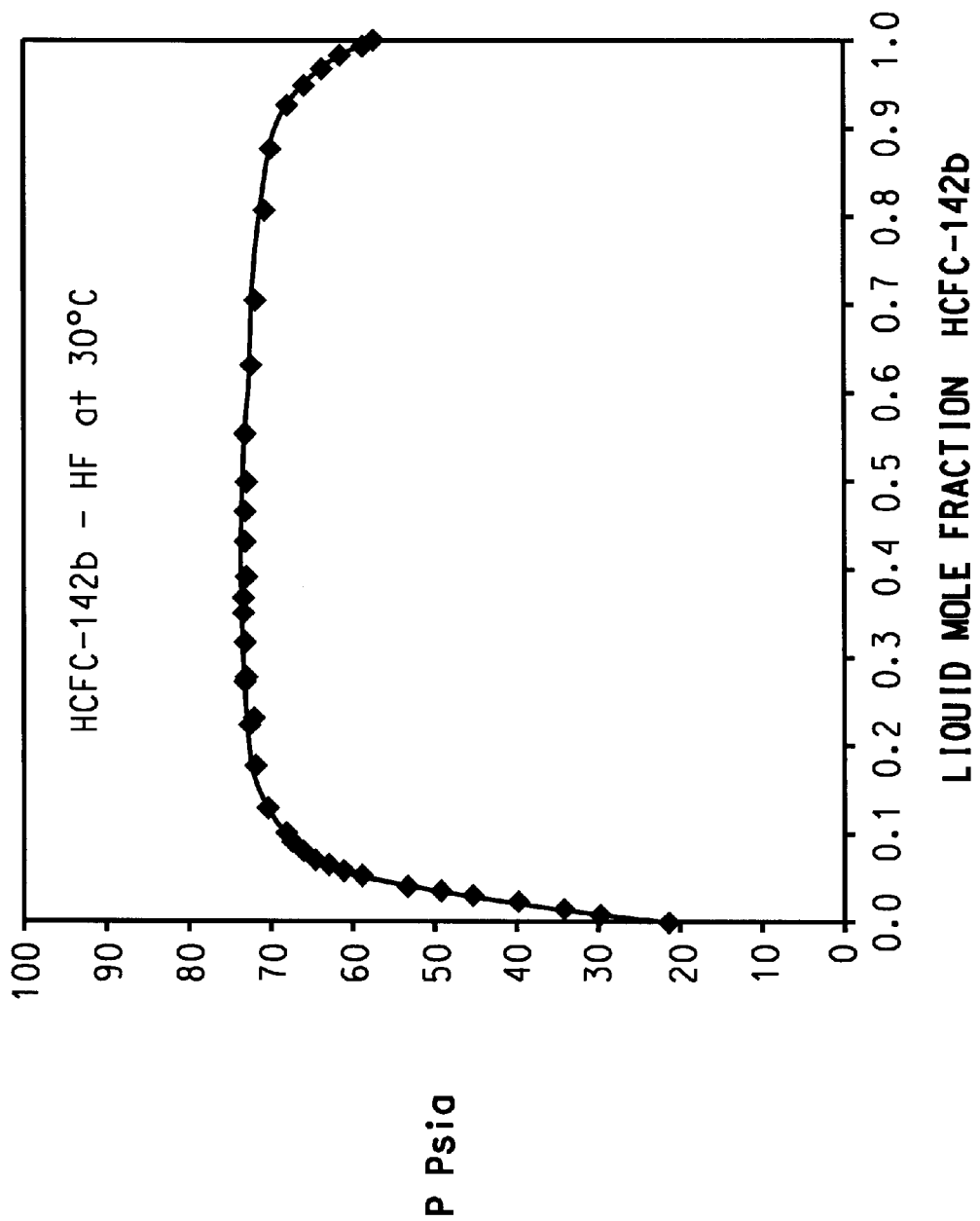
FIG. 9 is a graphical representation at about +30° C. of an azeotropic and azeotrope-like composition formed between HF and HCFC-142b.

Referring now to FIG. 9, FIG. 9 illustrates graphically the formation of an azeotropic or azeotrope-like composition consisting essentially of HF and HCFC-142b at a temperature of about +30° C., as indicated by mixtures of HF and HCFC-142b having a higher vapor pressure than either pure component at that temperature This system exhibits a maximum or peak pressure at +30° C. of about 74 psia, and contains about 51 mole percent HF and 49 mole percent CFC-114 in the vapor space of this higher pressure region. Accordingly, the present invention provides an azeotropic or azeotrope-like composition consisting essentially of about 51 mole percent HF and 49 mole percent HCFC-142b, having a boiling point of about +30° C. at 74 psia Based upon these findings, it has been calculated that an azeotropic or azeotrope-like composition of about 52 mole percent HF and 48 mole percent HCFC-142b is formed at a temperature of about −20° C. and 11 psia. Based upon these findings, it has been calculated that an azeotropic or azeotrope-like composition of about 50 mole percent HF and 50 mole HCFC-142b is formed at a temperature of about +40° C. and 92 psia. Accordingly, the present invention provides an azeotropic of azeotrope-like composition consisting essentially of from about 52 to 50 mole % HF and from 48 to 50 mole % HCFC-142b, said composition having a boiling point from about −20° C. at 10 psia to about +40° C. at 92 psia.

It has been been calculated that an azeotropic or azeotrope-like composition consisting of essentially about 24 mole percent HF and 76 mole percent propane is formed at a temperature of about −20° C. and 38 psia. It has been calculated that an azeotropic or azeotrope-like composition of about 39 mole percent HF and 61 mole propane is formed at a temperature of about +60° C. and 378 psia. Accordingly, the present invention provides an azeotropic of azeotrope-like composition consisting essentially of from about 24 to 39 mole % HF and from 76 to 61 mole % propane, said composition having a boiling point from about −20° C. at 38 psia to about +60° C. at 378 psia.

Example 3

This Example shows the effect of holding condensed HF and entraining agent mixtures at various temperatures. The "Initial Mixture" column in Table 2 indicates the mole % of HF and each of the entraining agents shown in an initial mixture, with the "initial Mixture" compositions as shown being azeotropic or azeotrope-like compositions of HF and the respective entraining agent that exist at a specific temperatures and pressures. Upon holding or bringing these mixtures as condensed liquids to the temperatures indicated in the second column of Table 2, the mixtures separate into two liquid layers.

For the purposes of the instant invention in which azeotropic or azeotrope-like initial mixtures comprising HF and an entraining agent are to be separated, Table 2 shows examples of temperatures at which the condensed initial azeotropic or azeotrope-like mixtures forms two liquid phases, and wherein one layer is enriched in HF and the other layer is enriched in organic relative to the initial azeotropic or azeotrope-like mixture. That is to say, these temperatures are examples of where the initial mixture separates into two layers such that the HF concentration is higher and lower in each of the liquid layers formed respectively, when compared to the initial mixture. Generally, the lower the temperature to which the initial mixture is cooled, the greater the efficiency of this separation. That is to say, the lower the temperature to which the initial mixture is cooled or held, the lower the residual organic and HF concentrations become in the HF and organic layers, respectively. By cooling azeotropic or azeotrope-like compositions sufficiently such that the mixture separates into two liquid layers having higher and lower HF concentrations than the initial composition, the layers thus formed may then optionally be processed by methods disclosed in the current specification.

TABLE 2

| Organic | Mole % In Initial Mixture | | Temp (° C.) | Mole % In HF Layer | | Mole % In Org. Layer | |
|---|---|---|---|---|---|---|---|
| | HF | Organic | | HF | Organic | HF | Organic |
| HCFC-142b | 42 | 58 | +20 | 85 | 15 | 31 | 69 |
|  | 42 | 58 | −20 | 91 | 9 | 14 | 86 |
| CFC-115 | 32 | 68 | +60 | 84 | 16 | 41 | 59 |
|  | 27 | 73 | −20 | 96 | 4 | 6 | 93 |
| CFC-114 | 81 | 19 | +100 | 97 | 3 | 14 | 86 |
|  | 90 | 10 | +20 | 99 | 1 | 2 | 97 |
| HCFC-124 | 43 | 57 | −10 | 75 | 25 | 35 | 65 |

Example 4

This Example shows the results of PTx measurements and NRTL calculations for azeotropic or azeotrope-like compositions found formed between HF and various compounds. We have found effective entraining agents for separating HF from HFC-245fa to be those compounds forming low-boiling azeotropic or azeotrope-like compositions with HF, which said compositions have higher maximum or peak pressures than that of HF/HFC-245fa azeotropic or azeotrope-like compositions when said azeotropic or azeotrope-like compositions are compared at the same temperature.

Table 3 compares the maximum or peak pressure of azeotropic or azeotrope-like compositions formed between HF and HFC-245fa with those formed between HF and a variety of other hydrocarbon, hydrofluorocarbon, hydrochlorocarbon, hydrochlorofluorocarbon, and fluorocarbon compounds. "Normal boiling point" refers to the normal or atmospheric boiling point of HFC-245fa or of the other hydrocarbon, hydrofluorocarbon, hydrochlorocarbon, hydrochlorofluorocarbon, hydrochlorocarbon or fluorocarbon compounds shown. The maximum or peak pressure of the azeotropic or azeotrope-like composition formed between HF and each of HFC-245fa, the hydrocarbon, hydrofluorocarbon, hydrochlorocarbon, hydrochlorofluorocarbon, hydrochlorocarbon or fluorocarbon compound indicated, at each of 0° C. and 50° C. as examples, is shown for comparison. We have found effective entraining agents for separating HF and HFC-245fa by distillation according to the instant invention to be those forming azeotropic or azeotrope-like compositions having peak or maximum pressures higher or greater than that of azeotropic or azeotrope-like compositions of HF and HFC-245fa when the pressures of the azeotropic or azeotrope-like compositions are compared at the same temperature.

TABLE 3

| | Normal Boiling Point (° C.) | Peak Pressure of Low-Boiling Azeotrope with HF (PSIA) | |
|---|---|---|---|
| | | At 0° C. | at 50° C. |
| HFC-245fa | 15 | +12 | +73 |

The following are entraining agents of the present process, as their HF-azeotropes have higher peak pressures than the HF/HFC-245fa azeotrope at the same temperature.

| Propane | −42 | +75 | +295 |
| n-Butane | −1 | +23 | +122 |
| CFC-12 (CCl$_2$F$_2$) | −30 | +52 | +215 |
| CFC-114 (CClF$_2$CClF$_2$) | +4 | +19 | +106 |
| CFC-114a (CCl$_2$FCF$_3$) | +3 | +20 | +106 |
| CFC-115 (CClF$_2$CF$_3$) | −39 | +71 | +295 |
| CFC-217ba (CF$_3$CClFCF$_3$) | −3 | +22 | +118 |
| HCFC-21 (CHFCl$_2$) | +9 | +16 | +92 |
| HCFC-22 (CHClF$_2$) | −41 | +75 | +285 |
| HCFC-124 (CF$_3$CHClF) | −12 | +28 | +141 |
| HCFC-124a (CHF$_2$CClF$_2$) | −10 | +28 | +141 |
| HCFC-133a (CClH$_2$CF$_3$) | +6 | +17 | +92 |
| HCFC-142b (CClF$_2$CH$_3$) | −9 | +26 | +127 |
| PFC-218 (CF$_3$CF$_2$CF$_3$) | −37 | +68 | — |
| Perfluorocyclobutane | −6 | +25 | +130 |
| Perfluoro-n-butane | −2 | +22 | +120 |

The following are not entraining agents in the present invention as their HF azeotropes have lower peak pressures than the HF/HFC-245fa azeotrope at the same temperature.

| CFC-112 (CCl$_2$FCCl$_2$F) | +93 | +7 | +43 |
| CFC-113 (CFCl$_2$CCl$_2$F) | +48 | +8 | +55 |
| HCFC-123 (CHCl$_2$CF$_3$) | +28 | +12 | +68 |
| HCFC-141b (CCl$_2$FCH$_3$) | +32 | +11 | +64 |
| HCC-150a (CHCl$_2$CH$_3$) | +57 | +8 | +50 |
| HCFC-151a (CHClFCH$_3$) | +16 | +12 | +72 |
| CFC-216aa (CF$_3$CClFCClF$_2$) | +33 | +10 | +64 |
| Methylene Chloride (CH$_2$Cl$_2$) | +40 | +9 | +58 |
| n-Hexane | +69 | +6 | +48 |
| n-Pentane | +36 | +11 | +66 |

What is claimed is:

1. A process for separating 1,1,1,3,3-pentafluoropropane (HFC-245fa) from hydrogen fluoride (HF), comprising:
   contacting a first mixture comprising 1,1,1,3,3-pentafluoropropane (HFC-245fa) and hydrogen fluoride (HF) with an entraining agent selected from the group consisting of hydrocarbons, chlorofluorocarbons, hydrochlorofluorocarbons and fluorocarbons, wherein said entraining agent has a normal boiling point of from about −50° C. to about 10° C., to form a second mixture,
   distilling the second mixture and thereby separating the 1,1,1,3,3-pentafluoropropane (HFC-245fa) from hydrogen fluoride (HF) and entraining agent, and
   recovering 1,1,1,3,3-pentafluoropropane (HFC-245fa).

2. The process of claim 1 wherein the first mixture comprises an azeotrope of 1,1,1,3,3-pentafluoropropane (HFC-245fa) and hydrogen fluoride (HF).

3. The process of claim 1 wherein the entraining agent is selected from the group consisting of chloro-1,1,1,2-tetrafluoroethane (HCFC-124), chloro-1,1,2,2-tetrafluoroethane (HCFC-124a), dichloro-1,1,2,2-tetrafluoroethane (CFC-114), dichloro-1,1,1,2-tetrafluoroethane (CFC-114a), 1-chloro-1,1-difluoroethane (HCFC-142b), chloropentafluoroethane (CFC-115), propane, n-butane, dichlorodifluoromethane (CFC-12), 2-chloro-1,1,1,2,3,3,3-heptafluoropropane (CFC-217ba), dichlorofluoromethane (HCFC-21), chlorodifluoromethane (HCFC-22), 2-chloro-1,1,1-trifluoroethane (HCFC-133a), octafluoropropane (PFC-218), perfluorocyclobutane and perfluoro-n-butane.

4. The process of claim 1 wherein the recovered 1,1,1,3,3-pentafluoropropane (HFC-245fa) is substantially-free of hydrogen fluoride (HF).

5. The process of claim 1 wherein the recovered 1,1,1,3,3-pentafluoropropane (HFC-245fa) contains less than about 1 part-per-million-by-weight (ppmw) hydrogen fluoride (HF).

6. The process of claim 1 wherein the recovered 1,1,1,3,3-pentafluoropropane (HFC-245fa) contains less than about 100 parts-per-billion-by-weight (ppbw) hydrogen fluoride (HF).

7. The process of claim 1 further comprising:

recovering an azeotropic or azeotrope-like third mixture comprising HF and entraining agent as distillation column overhead from said distilling step, cooling and thereby phase-separating the third mixture into a fourth mixture comprising an HF-enriched phase and a fifth mixture comprising an entraining agent enriched phase, and recycling the fifth mixture back to said contacting step.

8. The process of claim 1 further comprising:

recovering an azeotropic or azeotrope-like third mixture comprising HF and entraining agent as distillation column overhead from said distilling step, cooling and thereby phase-separating the third mixture into a fourth mixture comprising an HF-enriched phase and a fifth mixture comprising an entraining agent enriched phase, distilling the fourth and/or fifth mixtures under conditions sufficient to form an azeotrope or azeotrope-like sixth mixture comprising HF and entraining agent as distillation column overhead, recovering a seventh mixture comprising HF or entraining agent as distillation bottoms from said distilling step of the fourth and/or fifth mixtures, recycling the sixth mixture to said cooling step, and recycling the seventh mixture to said distilling step of the fourth and/or fifth mixtures.

* * * * *